US00PP14006P39

(12) United States Plant Patent
Bessho

(10) Patent No.: US PP14,006 P3
(45) Date of Patent: Jul. 22, 2003

(54) PETUNIA PLANT NAMED 'KAKEGAWA S60'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/989,538

(22) Filed: Nov. 21, 2001

(65) Prior Publication Data

US 2003/0097699 P1 May 22, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

PP8,888 P * 9/1994 Danziger

OTHER PUBLICATIONS

UPOV–ROM GTITM Computer Database, 2002/03, GTI Jouve Retrieval Software, citation for 'Kakegawa S60'.*

* cited by examiner

*Primary Examiner*—Bruce R. Campell
*Assistant Examiner*—Susan B. McCormick
(74) *Attorney, Agent, or Firm*—Jondle & Associates PC

(57) ABSTRACT

A Petunia plant particularly distinguished by its white flower color and creeping, mounding habit.

1 Drawing Sheet

Genus and species: Petunia hybrida.
Variety denomination: 'Kakegawa S60'.

BACKGROUND OF THE NEW PLANT

The present invention comprises a new and distinct cultivar of Petunia, botanically known as Petunia hybrida, and hereinafter referred to by the cultivar name 'Kakegawa S60'. 'Kakegawa S60' originated from a hybridization made in 1997 in Kakegawa, Japan. The female parent originated from a cross made in 1994 between an $F_4$ multiflora selection from the variety 'Dream White' and a dwarf multiflora pink breeding line. From several $F_1$ plants produced, three were selected for intercrossing. In 1995 the mass produced $F_2$ seed was sown and several dwarf multiflora white lines were selected for intercrossing to produce $F_3$ seed. Selection and intercrossing continued until the $F_5$ generation was produced, which was designated line 4-96b-1a-1 (not patented). The male parent originated from a cross made in 1994 between a dwarf multiflora white breeding line and a white flowered, creeping habit breeding line named 4UK-1 (not patented). Three $F_1$ plants were selected and intercrossed to produce $F_3$ seed. Selection and intercrossing continued until the $F_5$ generation was produced, which was designated line 4-197G-1a-14 (not patented).

Two hundred $F_1$ plants were transplanted to the field in Salinas, Calif. during the summer of 1998. Five lines were selected for further evaluation and vegetatively propagated. The five lines were propagated again in 1999 and evaluated for fixed characteristics and ease of propagation. Final selection of one line was made in Salinas, Calif. during the summer of 1999. The line was established as 'Kakegawa S60', and determined to have its characteristics firmly fixed.

'Kakegawa S60' has been found to retain its distinctive characteristics after two years and four cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
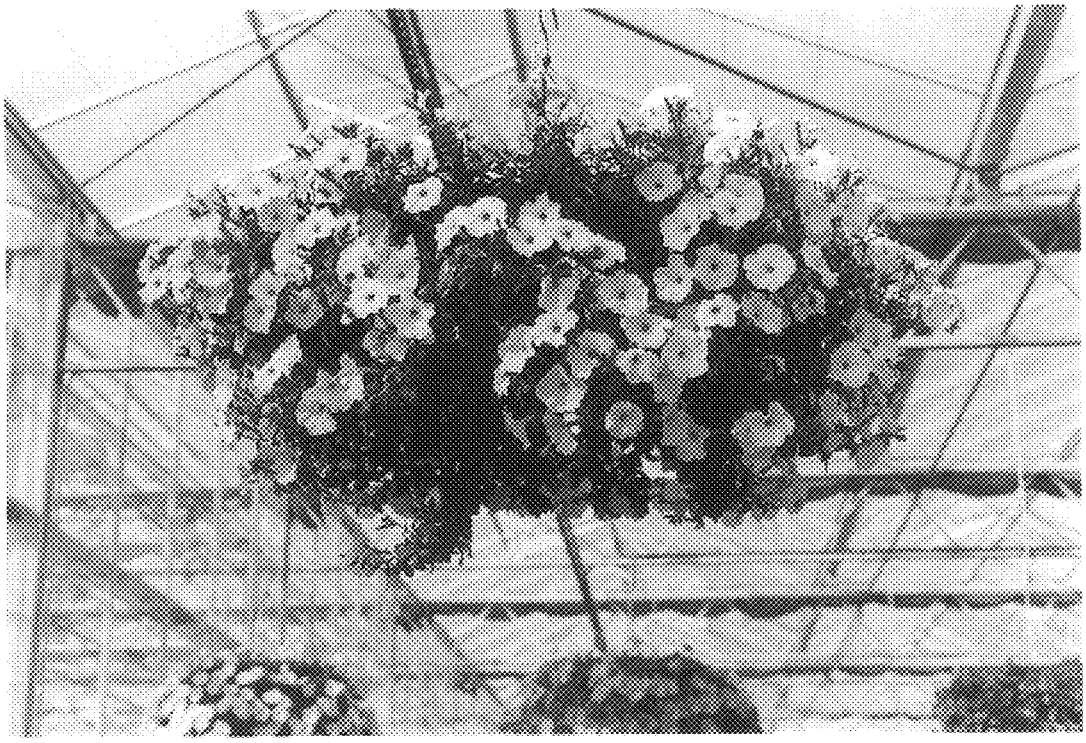
FIG. 1 shows the entire plant approximately eight weeks after transplanting a rooted cutting.
Figure 2:
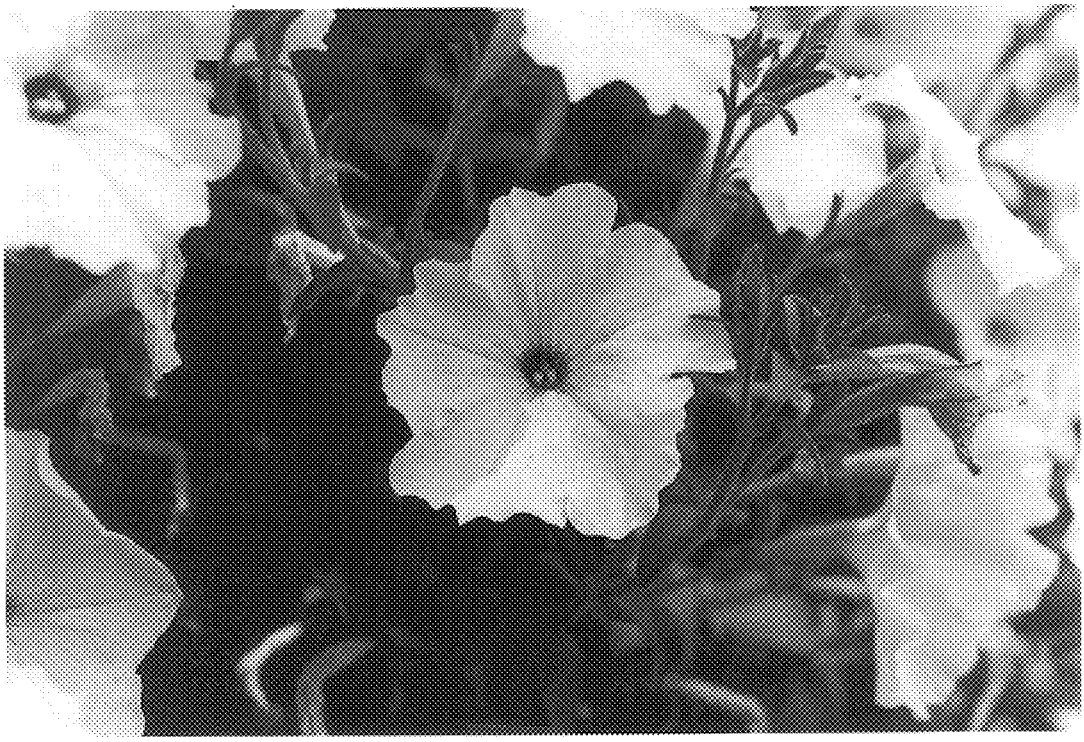
FIG. 2 shows the mature inflorescence.

The following detailed descriptions set forth the distinctive characteristics of 'Kakegawa S60'. The data which defines these characteristics were collected from asexual reproductions carried out in Salinas, Calif. Three plants from fully rooted 15 cm diameter pots were transplanted to one 50 cm diameter hanging baskets and grown in the same conditions. Data was collected on plants in 50 cm diameter pots eight weeks after rooted cuttings were transplanted. Color references are primarily to The R.H.S. Colour Chart of The Royal Horticultural Society of London (R.H.S.).

DESCRIPTION OF THE NEW PLANT

Classification:
- *Botanical.*—Petunia hybrida.
- *Commercial.*—Petunia.

Parentage:
- *Female parent.*—Breeding line 4-96b-1a-1 (not patented).
- *Male parent.*—Breeding line 4-197G-1a-14 (not patented).

Environmental conditions for plant growth:

Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C.

Growth:

*Habit.*—Branching, creeping.

*Form.*—Descending.

*Plant size.*—45 cm total diameter and 25 cm total height.

*Flowering habit.*—Indeterminate.

*Time to initiate root development.*—7 days after sticking cuttings.

*Time to bloom from propagation.*—4–6 weeks after rooting when grown in 10–15 cm diameter plastic pots.

*Life cycle.*—Annual.

Stems:

*Color.*—Yellow-green (RHS 145A).

*Description.*—Round.

*Diameter.*—0.2 to 0.3 mm.

*Internode length.*—4.0 cm.

Leaves:

*Arrangement.*—Opposite.

*Apex.*—Mucronate.

*Base.*—Oblique.

*Color.*—Upper surface is green (RHS 139A) and lower surface is green (RHS 138C).

*Margin.*—Entire.

*Size.*—Length is 6.0–6.5 cm and width is 4.0–4.2 cm.

*Shape.*—Ovate.

*Texture.*—Coarse.

*Venation.*—Pinnate.

*Pubescence.*—Present, clear.

Buds:

*Bud color.*—Yellow-green (RHS 144C).

*Bud diameter.*—5.0 mm.

*Bud length.*—1.8 cm.

Flowers:

*Calyx.*—5 sepals; 2.0 cm×0.4 cm (length×width).

*Corolla.*—5 petals, fused.

*Flower diameter.*—6.0–7.5 cm.

*Fragrant.*—Yes.

*Inflorescence type.*—Solitary.

*Pistil.*—Compound.

*Ovary.*—Superior, parietal placentation.

*Stamens.*—5 total with two long and three short; yellow-green (RHS 150D).

*Style.*—Green (RHS 143C).

*Peduncle.*—4.0–5.0 cm×0.1 mm (length×width); pubescent.

*Petal color.*—Limbs: upper — white (RHS 155B); lower — white (RHS 155B). Tube — Inner — yellow-green (RHS N144D) with purple (RHS 79B) veins; Outside is yellow-green (RHS 144D) with yellow-green (RHS 144B) veins.

*Petal margin.*—Smooth.

*Petal pubescence.*—Absent.

*Tube throat diameter.*—0.7 mm.

*Pollen color.*—Yellow (RHS 8C).

*Produces seed.*—Yes; grey-orange (RHS 172B); <1.0 mm diameter; seed coat has netted pattern, 8–10,000 seeds/gram.

Disease and Insect Resistance

No susceptibility to diseases or insects noted to date.

Comparison with Known Cultivars

'Kakegawa S60' is most similar to the variety 'Cascadia Choice' but differs in the following areas: 'Kakegawa S60' flowers are larger in diameter when fully expanded than 'Cascadia Choice'. The width of the corolla tube at the throat is narrower for 'Kakegawa S60' than for 'Cascadia Choice'. 'Cascadia Choice' has a purple or reddish ring at the corolla throat where 'Kakegawa S60' simply transitions from white petals to a greenish yellow tube.

Comparison with Parental Cultivars

Table 1 below lists some traits from the parental cultivars as compared to the present invention.

TABLE 1

| Characteristic | 'Kakegawa S57' | 4-96b-1a-1 (female) | 4-197G-1a-14 (male) |
|---|---|---|---|
| Plant Habit | Creeping | Dwarf and compact | Creeping |
| Flower Size | Medium | Grandiflora | Medium |
| Flower Petal Color | White | White | White |

I claim:

1. A new and distinct Petunia plant as shown and described herein.

* * * * *